United States Patent [19]

Althuis et al.

[11] 4,310,668

[45] Jan. 12, 1982

[54] INTERMEDIATES TO 1,9-DIHYDROXYOCTAHYDROPHENANTHRENES

[75] Inventors: Thomas H. Althuis, Groton; Charles A. Harbert, Waterford; Michael R. Johnson, Gales Ferry; Lawrence S. Melvin, Jr., Ledyard, all of Conn.

[73] Assignee: Pfizer Inc., New York, N.Y.

[21] Appl. No.: 218,966

[22] Filed: Dec. 22, 1980

Related U.S. Application Data

[62] Division of Ser. No. 78,475, Sep. 24, 1979, Pat. No. 4,268,692, which is a division of Ser. No. 851,503, Nov. 14, 1977, Pat. No. 4,188,495.

[51] Int. Cl.³ ............... C07D 213/50; C07D 213/55
[52] U.S. Cl. .................... 546/204; 260/326.33; 544/130; 544/131; 544/155; 544/360; 544/380; 546/188; 546/189; 546/190; 546/194; 546/208; 546/281; 546/285; 560/134; 560/139
[58] Field of Search ............... 546/204, 285, 188, 189, 546/190, 194, 208, 281; 544/130, 131, 155, 360, 380; 260/326.33, 326.43; 560/134, 139

[56] References Cited

U.S. PATENT DOCUMENTS 2,750,382  6/1956  Bible et al. ............... 546/204 X
2,764,616  9/1956  Hoehn et al. ............ 546/285 X

OTHER PUBLICATIONS

*Chemical Abstracts*, 50:11356e (1956) [Kalvoda, J. et al., *Helv. Chim. Acta*, 38, 1847–1856 (1955)].

*Primary Examiner*—Richard A. Schwartz
*Attorney, Agent, or Firm*—Connolly and Hutz

[57] ABSTRACT

Compounds of the formula wherein $R_1$ is hydrogen, benzyl, benzoyl, alkanoyl of 1 to 5 carbon atoms or $-CO-(CH_2)_p-NR'R''$ wherein p is 0 or an integer from 1 to 4; each of R' and R'' when taken individually is hydrogen or alkyl of 1 to 4 carbon atoms; R' and R'' when taken together with the nitrogen to which they are attached form a 5- or 6-membered heterocyclic ring selected from piperidino, pyrrolo, pyrrolidino, morpholino and N-alkylpiperazino having from 1 to 4 carbon atoms in the alkyl group;

$R_2$ is selected from hydrogen, alkanoyl of 1 to 6 carbon atoms and benzoyl;

$R_3$ is selected from hydrogen, methyl and ethyl;

$R_4$ is selected from hydrogen, alkyl of 1 to 6 carbon atoms and benzyl;

Z is selected from:
(a) alkylene having from one to nine carbon atoms;
(b) $-(alk_1)_m-X-(alk_2)_n-$ wherein each of $(alk_1)$ and $(alk_2)$ is alkylene having from 1 to 9 carbon atoms, with the proviso that the summation of carbon atoms in $(alk_1)$ plus $(alk_2)$ is not greater than 9;

m and n are each 0 or 1;
X is selected from O, S, SO and $SO_2$; and
W is selected from hydrogen, methyl, pyridyl, piperidyl, phenyl, monochlorophenyl, monofluorophenyl and wherein $W_1$ is selected from hydrogen, phenyl, monochlorophenyl and monofluorophenyl; a is an integer from 1 to 5 and b is 0 or an integer from 1 to 4, with the proviso that the sum of a and b is not greater than 5.

Compounds I and II are useful as analgesics. Compound III is useful as an intermediate for the preparation of Compounds I and II. Intermediates for the preparation of I, II and III are disclosed. A process for the use of compounds I and II to produce analgesia is also described.

9 Claims, No Drawings

INTERMEDIATES TO 1,9-DIHYDROXYOCTAHYDROPHENANTHRENES

CROSS REFERENCE TO RELATED APPLICATION

This application is a division of application Ser. No. 078,475 filed Sept. 24, 1979, now U.S. Pat. No. 4,268,692, which in turn is a division of application Ser. No. 851,503 filed Nov. 14, 1977, and now U.S. Pat. No. 4,188,495.

BACKGROUND OF THE INVENTION

This invention relates to novel 1,9-dihydroxyoctahydrophenanthrenes and 1-hydroxyoctahydrophenanthren-9-ones and derivatives thereof having analgesic properties useful for administration to mammals including humans, and to intermediates useful for the preparation of said compounds.

Despite the current availability of a number of analgesic agents, the search for new and improved agents continues, thus pointing to the lack of an agent useful for the control of broad levels of pain and accompanied by a minimum of side-effects. The most commonly used agent, aspirin, is of no practical value for the control of severe pain and is known to exhibit various undesirable side-effects. Other, more potent analgesic agents such as d-propoxyphene, codeine, and morphine, possess addictive liability. The need for improved and potent analgesic agents is, therefore, evident.

The analgesic properties of 9-nor-9β-hydroxyhexahydrocannabinol and of other cannabinoid structures, such as $\Delta^8$-tetrahydrocannabinol ($\Delta^8$-THC) and its primary metabolite, 11-hydroxy-$\Delta^8$-THC, have been reported by Wilson and May, *Absts. Papers, Am. Chem. Soc.*, 168 Meet., MEDI 11 (1974), *J. Med. Chem.*, 17, 475-476 (1974), and *J. Med. Chem.*, 18, 700-703 (1975).

U.S. Pat. Nos. 3,507,885 and 3,636,058, issued Apr. 21, 1970 and Jan. 18, 1972, respectively, describe various 1-hydroxy-3-alkyl-6H-dibenzo-[b,d]pyrans having at the 9-position substituents such as oxo, hydrocarbyl and hydroxy or chloro, hydrocarbylidene, and intermediates therefor.

U.S. Pat. No. 3,649,650, issued Mar. 14, 1972, discloses a series of tetrahydro-6,6,9-trialkyl-6H-dibenzo[b,d]pyran derivatives having at the 1-position an ω-dialkylaminoalkoxy group active as psychotherapeutic agents.

German Specification No. 2,451,934, published May 7, 1975, describes 1,9-dihydroxyhexahydrodibenzo[b,d]pyrans and certain 1-acyl derivatives thereof having at the 3-position an alkyl or alkylene group, as hypotensive, psychotropic, sedative and analgesic agents. The precursor hexahydro-9H-dibenzo[b,d]pyran-9-ones used in their preparation, and which are reported to have the same utility as the corresponding 9-hydroxy compounds, are described in German Specification No. 2,451,932, published May 7, 1975.

U.S. Pat. No. 3,856,821, issued Dec. 24, 1974, describes a series of 3-alkoxy substituted dibenzo[b,d]pyrans having antiarthritic, antiinflammatory and central nervous system activity.

Bergel et al., *J. Chem. Soc.*, 286-287 (1943) investigated the replacement of the pentyl group at the 3-position of 7,8,9,10-tetrahydro-3-pentyl-6,6,9-trimethyl-6H-dibenzo[b,d]pyran-1-ol by alkoxy (butoxy, pentyloxy, hexyloxy and octyloxy) and found that it led to biological inactivity. The hexyloxy derivative was reported to exhibit feeble hashish activity at 10 to 20 mg./kg. The remaining ethers showed no activity in doses up to 20 mg./kg.

In a more recent study, Loev et al., *J. Med. Chem.*, 16, 1200-1206 (1973) report a comparison of 7,8,9,10-tetrahydro-3-substituted-6,6,9-trimethyl-6H-dibenzo[b,d]-pyran-1-ols in which the 3-substituent is $-OCH(CH_3)C_5H_{11}$; $-CH_2CH(CH_3)C_5H_{11}$; or $-CH(CH_3)C_5H_{11}$. The ether side chain containing compound was 50% less active in central nervous system activity than the corresponding compound in which the alkyl side chain is directly attached to the aromatic ring, rather than through an intervening oxygen atom; and 5 times as active as the compound in which oxygen is replaced by methylene.

Co-pending U.S. patent application Ser. No. 819,471 filed July 27, 1977 discloses a series of 1,9-hydroxyhexahydrodibenzo[b,d]pyrans and intermediates therefor having analgesic and other therapeutic activities. Co-pending U.S. patent application Ser. No. 777,928 filed Mar. 15, 1977 discloses a series of 1,9-dihydroxyoctahydrodibenzo[c]quinolines and intermediates therefor also having analgesic and other therapeutic activities.

Mechoulam and Edery in "Marijuana", edited by Mechoulam, Academic Press, New York, 1973, page 127, observe that major structural changes in the tetrahydrocannabinol molecule seem to result in steep reductions in activity.

Paton, in *Annual Review of Pharmacology*, 15, 192 (1975) presents generalizations on structure-action relationships among cannabinoids. The presence of the gem dimethyl group in the pyran ring is critical for cannabinoid activity and substitution of N for O in the pyran ring removes activity. Paton also reports that substitution of a $-CH_2-$ group for oxygen in the pyran ring to produce phenanthrenes has not been examined.

SUMMARY OF THE INVENTION

The present invention relates to novel compounds of the formulae

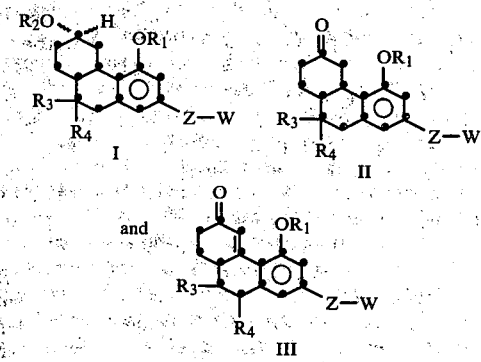

wherein $R_1$ is hydrogen, benzyl, benzoyl, alkanoyl of 1 to 5 carbon atoms or $-CO-(CH_2)_pNR'R''$ wherein p is 0 or an integer from 1 to 4; each of $R'$ and $R''$ when taken individually is hydrogen or alkyl of 1 to 4 carbon atoms; $R'$ and $R''$ when taken together with the nitrogen to which they are attached form a 5- or 6-membered heterocyclic ring selected from piperidino, pyrido, pyrrolidino, morpholino and N-alkylpiperazino having from 1 to 4 carbon atoms in the alkyl group;

$R_2$ is selected from hydrogen, alkanoyl of 1 to 6 carbon atoms and benzoyl;

$R_3$ is selected from hydrogen, methyl and ethyl;

$R_4$ is selected from hydrogen, alkyl of 1 to 6 carbon atoms and benzyl;

Z is selected from:

(a) alkylene having from one to nine carbon atoms;

(b) —$(alk_1)_m$—X—$(alk_2)_n$— wherein each of $(alk_1)$ and $(alk_2)$ is alkylene having from 1 to 9 carbon atoms, with the proviso that the summation of carbon atoms in $(alk_1)$ plus $(alk_2)$ is not greater than 9;

m and n are each 0 or 1;

X is selected from O, S, SO and $SO_2$; and

W is selected from hydrogen, methyl, pyridyl, piperidyl, phenyl, monochlorophenyl, monofluorophenyl and

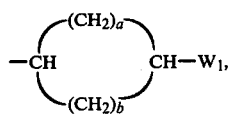

wherein $W_1$ is selected from hydrogen, phenyl, monochlorophenyl and monofluorophenyl; a is an integer from 1 to 5 and b is 0 or an integer from 1 to 4, with the proviso that the sum of a and b is not greater than 5.

Compounds of formulae I and II are effective as analgesic agents and are non-narcotic and free of addiction liability. These compounds also have utility as antihypertensives, immunosuppressants, tranquilizers, diuretics and as anti-anxiety drugs and as agents for the treatment of glaucoma. Compounds of formula II are useful as intermediates for the formation of analgesic agents of formula I. Compounds of formula III are useful as intermediates for the formation of compounds of the formulae I and II.

Of particular interest as analgesics are the compounds of formula I as defined above. In such compounds $R_1$ and $R_2$ are preferably hydrogen or alkanoyl and $R_3$ and $R_4$ are preferably hydrogen, methyl, or ethyl. One preferred group for Z is alkylene of 4 to 9 carbon atoms, most preferably —$CH(CH_3)$—$(CH_2)_3$—. A further particularly preferred alkylene group for Z is 1,2-dimethylhexylene, especially where W is methyl. Another preferred group for Z is $(alk_1)_m$—X—$(alk_2)_n$, especially $(alk_1)_m$—O—$(alk_2)_n$. Most preferably Z is —O—$(alk_2)$ where $(alk_2)$ has from 4 to 9 carbon atoms, especially —O—$CH(CH_3)$—$(CH_2)_3$—. Preferred groups for W are hydrogen, methyl and phenyl, with phenyl being especially preferred. The compound of formula I where $R_1$ and $R_2$ are each hydrogen, $R_3$ and $R_4$ are each methyl, Z is —O—$CH(CH_3)$—$(CH_2)_3$— and W is phenyl is a compound of particular interest for its utility as an analgesic agent. A further preferred compound of formula I having analgesic activity is that where $R_1$, $R_2$, $R_3$ and $R_4$ are each hydrogen, Z is —O—$CH(CH_3)$—$(CH_2)_3$— and W is phenyl.

Compounds of formula II are intermediates for the preparation of the corresponding compounds of formula I and are also useful as analgesic agents. Preferred substituents $R_1$, $R_2$, $R_3$, $R_4$, Z and W are those described above for the corresponding compounds of formula I.

Compounds of formula III are useful as intermediates for the preparation of the corresponding compounds of formulae I and II. Preferred intermediates are those useful for the preparation of the preferred compounds of formulae I and II described above herein. Thus, preferred values of the substituents $R_1$, $R_2$, $R_3$, $R_4$, Z and W are those described above for the preferred compounds of formula I.

Also disclosed is a process for producing analgesia in a mammal which comprises administering to the mammal an analgesia producing quantity of a compound of formulae I or II. The analgesia-producing compound is most preferably of formula I. Compounds of formula II are also preferred compounds for use in the present process. Preferred compounds of either formula I or II for the use in the above process to produce analgesia in the mammal are those having the preferred groups of $R_1$, $R_2$, $R_3$, $R_4$, Z and W as described above herein.

Further useful intermediates for the preparation of compounds of formulae I, II and III are also disclosed. Such useful intermediates include those of the formulae

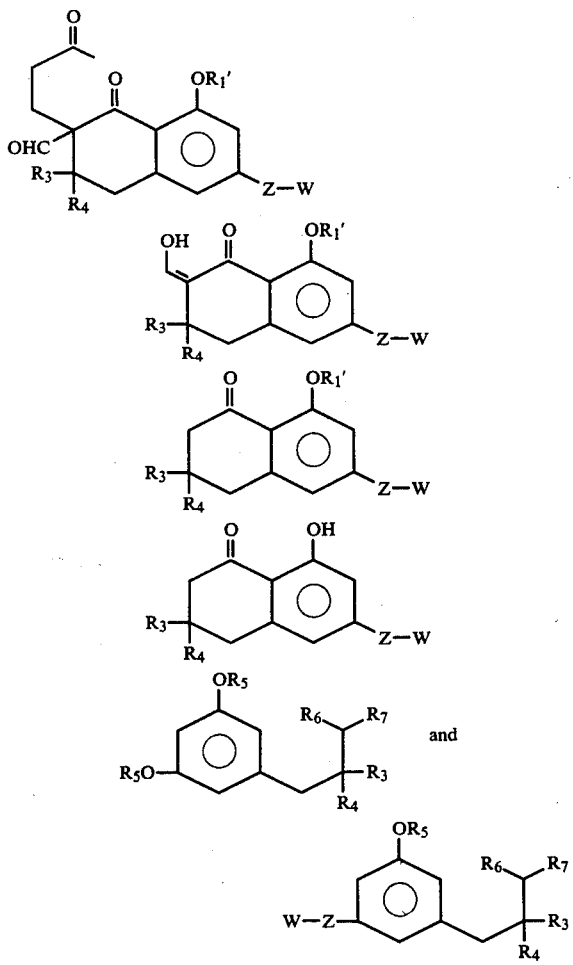

wherein $R_1'$ is hydrogen, alkanoyl of 1 to 6 carbon atoms and benzoyl; $R_3$, $R_4$, Z and W are as defined above;

$R_5$ is selected from hydrogen, alkyl of 1 to 6 carbon atoms and benzyl, with the proviso that when Z is —O—$(alk_2)$, $R_5$ is benzyl; and $R_6$ and $R_7$ are each selected from —CN and —$COOR_0$, wherein $R_0$ is alkyl of 1 to 3 carbon atoms.

Preferred intermediates of these formulae are those useful for preparing the preferred compounds of formulae, I, II and III as previously described.

DETAILED DESCRIPTION OF THE INVENTION

The compounds of formula III are readily prepared from the corresponding 3,3—(R$_3$R$_4$)—6—(Z—W-)—8—(OR$_1$′)—1-tetralones of formula IV, the reaction sequence being shown in reaction scheme 1.

REACTION SCHEME 1

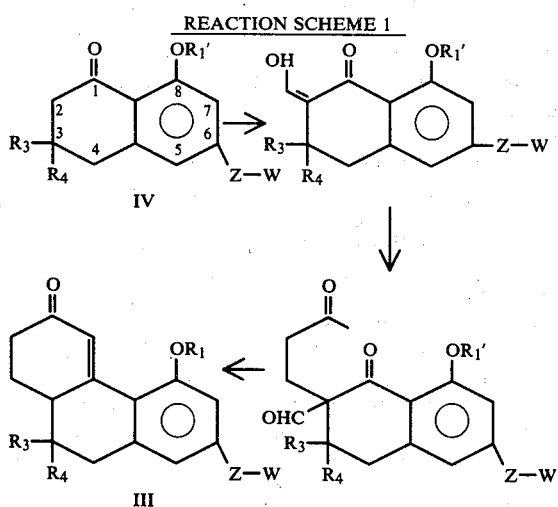

The 3,3—(R$_3$R$_4$)—6—(Z—W)—(OR′$_1$)—1—tetralone is first reacted with ethyl formate in the presence of an alkali metal hydride such as sodium hydride. The resulting 2-hydroxymethylene-3,3—R$_3$R$_4$—6—(Z—W-)—8—(OR′$_1$)—1—tetralone is reacted with methyl vinyl ketone in the presence of a base, such as an alkali metal hydroxide or alkoxide or a tertiary organic amine, such as triethylamine, to effect Michael addition. The formed 2-(3′—oxobutyl)—2—formyl—3,3—(R$_3$R$_4$)—6—(Z—W)—8—(OR′$_1$)—1—tetralone is then treated with a base, for example an alkali metal hydroxide or alkoxide to complete aldol cyclization to form the desired compound of formula III.

Compounds of formula III are converted by Birch reduction to the corresponding compounds of formula II using an alkali metal such as lithium, sodium or potassium and ammonia. The reduction may be conducted at a temperature of about −35° C. to about −80° C. Reduction of compounds of formula II occurs with an excess of the alkali metal or can be carried out with a metal hydride to afford the compounds of formula I where R$_2$ is hydrogen. Suitable metal hydrides include lithium aluminum hydride, lithium borohydride and sodium borohydride. Sodium borohydride is a preferred reducing agent for this reaction since it reacts slowly enough with hydroxylic solvents to allow their use as solvents. Suitable solvents include methanol, ethanol and water. Temperatures between about 0° and 30° C. may be used, but preferably temperatures below 0° C. and down to about −70° C. are employed. At higher temperatures reaction of the sodium borohydride with the hydroxylic solvent may occur. If desired, higher reaction temperatures may be employed by use of isopropyl alcohol, or the dimethyl ether of diethylene glycol as solvent. When lithium borohydride or lithium aluminum hydride are used as the reducing agent, anhydrous conditions and non-hydroxylic solvents are employed at temperatures between about −70° C. and about 0° C. Suitable solvents include 1,2-dimethoxyethane, tetrahydrofuran, diethyl ether and the dimethyl ether of diethylene glycol.

Esters of compounds of formulae II and III wherein R$_1$ is alkanoyl, and esters of compounds of formula I wherein each of R$_1$ and R$_2$ is alkanoyl, are readily prepared by reacting the corresponding compounds wherein R$_1$ and R$_2$ are hydrogen with the appropriate alkanoic acid in the presence of a condensing agent such as dicyclohexylcarbodiimide. Alternatively, they may be prepared by reaction with the appropriate alkanoic acid chloride or anhydride in the presence of a base such as pyridine. Similarly, compounds of formulae I, II and III where R$_1$ is —CO—(CH$_2$)$_p$—NR′R″ are prepared by analagous reactions, for example by condensation with an acid of the formula HOOC—(CH$_2$-)$_p$—NR′R″. Compounds of formula I in which only the 9-hydroxy group is acylated are obtained by mild hydrolysis of the corresponding 1,9-diacyl derivative, advantage being taken of the greater ease of hydrolysis of the phenolic acyl group. Compounds of formula I in which only the 1-hydroxy group is esterified are obtained by borohydride reduction of the corresponding formula II ketone esterified at the 1-position. The thus produced formula I compound having 1-acyl-9-hydroxy substitution or 1-hydroxy-9-acyl substitution can then be acylated further with a different acylating agent to produce a diesterified compound of formula I in which the ester group at the 1- and the 9-positions are different.

The 3,3—(R$_3$R$_4$)—6—(Z—W)—8—(OR′$_1$)—1—tetralone of formula IV starting material for the above reaction sequence may be synthesized from an appropriate 5—(Z—W)—3—(OY$_1$)—benzyl halide, where Y$_1$ is alkyl of 1 to 4 carbon atoms, preferably methyl, benzyl or substituted benzyl. The reaction sequence is shown in reaction scheme 2. The (OY$_1$)—substituent serves as a protected hydroxyl group, the protecting alkyl or aryl group being removed later in the synthesis. When Z is alkylene, Y$_1$ is desirably methyl or benzyl. When Z is (alk$_1$)$_m$—X—(alk$_2$)$_n$, Y$_1$ is preferably benzyl or substituted benzyl, since it can be subsequently removed to form a hydroxyl group without detriment to the Z group. A Grignard reagent is first prepared by reacting the substituted benzyl halide with powdered magnesium in a suitable solvent such as tetrahydrofuran. This is then reacted with an appropriate alkylidene malonate derivative, as shown in scheme 2. The alkylidene malonate derivative may be formed by the condensation of a suitable aldehyde of the formula R$_3$CHO or ketone of the formula R$_3$R$_4$CO, with an alkyl cyanoacetate, dialkyl malonate or dicyano malonate. Preferably, the alkyl group of the malonate ester derivative is of 1 to 3 carbon atoms. The reaction is effected in a suitable solvent such as tetrahydrofuran at a temperature below about 10° C.

REACTION SCHEME 2

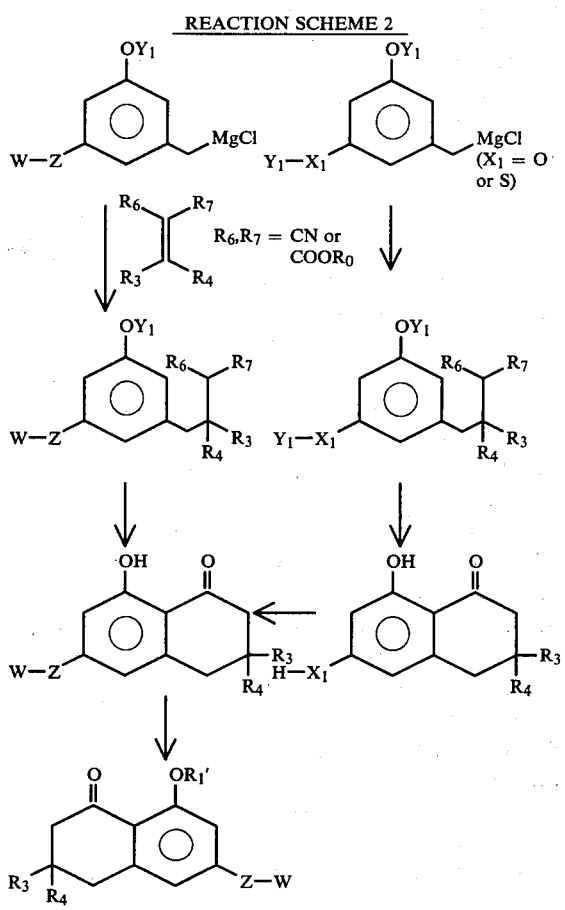

The product is hydrolyzed by treatment with an alkali metal hydroxide in alcohol solution, preferably sodium or potassium hydroxide in methanol or ethanol, followed by acidification. Cyclization to form the 3,3—($R_3R_4$)—6—(Z—W)—8—hydroxy-1-tetralone is conveniently effected by refluxing with aqueous hydrogen bromide in glacial acetic acid, decarboxylation, cyclization and conversion of alkoxy or aryloxy to hydroxy by removal of the $Y_1$ group is effected in the one step. These reactions may be effected stepwise, if desired. The 3,3—($R_3R_4$)—6—(Z—W)—8—hydroxy-1-tetralone may be used as a starting material for the synthesis of compounds of formulae I, II and III. Preferably, however, the 8-hydroxy group is protected by reaction with a benzyl halide, methyl iodide or dimethyl sulfate. A preferred protecting group when Z—W is joined to the tetralone ring by oxygen or sulfur is benzyl.

In an alternative method, the Z—W substituent may be introduced during the reaction sequence, as also shown in reaction scheme 2. This is a particularly useful and preferred method for preparation of compounds having an oxygen or sulfur atom linking the Z group to the tetralone ring. Suitable starting materials are 3,5—($OY_1$)—benzyl halides and the corresponding 3,5—(-$SY_1$)—benzyl halides. $Y_1$ is as previously defined and is preferably methyl or benzyl. The substituted benzyl halide is converted to a Grignard reagent, reacted with an appropriate alkylidene malonate derivative and cyclized, as described previously. The Z—W group is then introduced by reaction with one equivalent of an appropriate Z—W methane sulfonate, which reacts with the 6-hydroxy or 6-thiol group of the tetralone. The reaction is conveniently effected in the presence of a base, preferably an alkali metal hydride such as sodium or potassium hydride, or an alkali metal carbonate such as potassium or sodium carbonate, in a suitable organic solvent such as dimethyl formamide or acetone. The reaction is preferably conducted in an inert atmosphere at temperatures between about 60° C. and 100° C. The Z—W methane sulfonate is a preferred reagent for introduction of the Z—W group in the 6-position of the tetralone. However, any reagent that will react with the —OH or —SH group and allow introduction of the Z—W group at the 6-position of the cyclized intermediate may be used. Suitable alternative reagents include the corresponding Z—W halides, preferably the bromide or iodide.

Compounds where the Z group contains —SO— or $SO_2$ groups are conveniently prepared by oxidation of compounds containing sulfur in the appropriate position of the 6—(Z—W)—substituent of the tetralone, which are prepared by the methods described above. The oxidation may be effected at any subsequent stage of the synthesis but most conveniently compounds of formula II are oxidized. Compounds of formula III may also be oxidized to convert S to SO or $SO_2$ in the Z group. The oxidation to SO may be carried out by using one equivalent of a peracid such as m-chloroperbenzoic acid, perbenzoic acid and other such acids, which may be prepared in situ from a mixture of the corresponding carboxylic acid and hydrogen peroxide. The reaction is conducted at a temperature between about 0° C. and 25° C., preferably about 0° C. and 10° C. Using two equivalents of a peracid the corresponding compound where Z contains an $SO_2$ group are obtained.

5—(Z—W)—3—($OY_1$)—substituted benzyl halides useful for the preparation of the tetralone starting materials are known in the art or may be synthesized by the following procedures. 3-methoxy isophthalaldehydic acid methyl ester is prepared from 3-methoxy isophthalic acid dimethyl ester by reduction with diisobutyl aluminum hydride. The formyl group may then be reacted with Wittig reagents to introduce the Z—W group. By choice of appropriate reagents straight or branched alkylene groups can be introduced. The Wittig reaction is effected by use of an alkylidene triphenylphosphorane. The Z—W substituent is formed by catalytic reduction of the unsaturated side chain using platinum or palladium on carbon as a catalyst. Reduction of the ester function with excess lithium aluminum hydride in ether at reflux temperature and acidification yields the corresponding 1—(Z—W)—3-methoxy-benzyl alcohol. The latter is converted to the corresponding benzyl halide by reaction with a thionyl halide, preferably thionyl chloride, at reflux temperature. The formed substituted benzyl halide may be purified if desired by recrystallization, column chromatography or vacuum distillation. For compounds with an α-branch in the Z—W side chain, the 3-methoxy isophthalaldehydic acid dimethyl ester is hydrolyzed by dilute acid or base to yield the half ester acid. The carboxyl group is reacted with thionyl chloride to form the acid chloride, which is then reacted with diethyl malonate as the ethoxy magnesium salt. Hydrolysis by dilute acid and decarboxylation produces methyl 3-methoxy-5-acetyl benzoate. The carbonyl group of the acetyl substituent is then converted to the Z—W group by the Wittig reaction and the carbomethoxy group subsequently reduced to form the benzyl halide by the sequences described above.

Substituted benzyl halides of the type

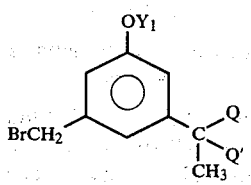

where Q' is hydrogen or methyl and Q is alkyl, alkyloxyalkyl and alkylthioalkyl may be prepared by Friedel-Crafts alkylation of m-cresol. Meta substitution is effected under forcing conditions using excess aluminum chloride catalyst and reflux temperatures, see "Anhydrous Aluminum Chloride in Organic Chemistry", Reinhold Publishing Corporation, New York, 1941, page 181. The phenolic group is conveniently protected at this time in anticipation of the formation of a Grignard reagent later in the synthesis. This can be done by reaction with, for example, methyl iodide, dimethyl sulfate or benzyl chloride. Subsequent bromination using N-bromosuccinimide yields the desired substituted benzyl bromide.

A further method of preparing the substituted benzyl halides useful for preparation of the tetralone starting materials is from 1-acetyl-3-nitro-5-caboalkoxy-benzene, where alkoxy is of 1 to 4 carbon atoms. See Chem. Abs. 57 13663a, Zh. Obshch Khim 32, 293 (1962). The carbonyl group of the acetyl substituent is reacted with Wittig reagents to introduce the Z—W side chain as previously described, followed by catalytic reduction over platinum or palladium on carbon. The reduction is effective to reduce both the double bond in the Z group and to convert the nitro group to amino. Diazotisation of the amino group with hydrochloric acid and sodium nitrite in water yields the corresponding phenol which is then protected by reaction with methyl iodide, dimethyl sulfate or benzyl chloride. The ester function is then reduced with lithium aluminum hydride to yield the benzyl alcohol. The corresponding benzyl halide is prepared by reaction of the benzyl alcohol with thionyl chloride or phosphorous pentachloride.

3-methoxy isophthalaldehydic acid methyl ester, 3-methoxy-5-acetyl benzoate and analagous compounds may also be used in an alternative synthesis of the substituted tetralone starting materials of formula IV, which is especially useful when W is a nitrogen-containing heterocyclic group. It is also a preferred method for preparing compounds where Z is —(alk$_1$)$_m$—S—(alk$_2$)$_n$— and m is one. In this method, the carbonyl function of the formyl or acetyl substituent is first protected by forming an acetal or ketal. This may be effected by reaction with a suitable glycol such as, but not limited to, ethylene glycol in the presence of a catalytic amount of a strong acid such as p-toluenesulfonic acid or sulfuric acid. The protected compound is then converted to a substituted benzyl halide, via reduction to the substituted benzyl alcohol and subsequent reaction with a thionyl halide. The protected benzyl halide so formed is converted to a Grignard reagent, reacted with an appropriate alkylidene malonate derivative, followed by hydrolysis and cyclization, as described in detail for these reaction steps previously, to form a 3,3—(R$_3$R$_4$)—8—hydroxy-1-tetralone having at the 6-position the acetal- or ketal-protected formyl or acetyl group, depending on the starting material. The carbonyl function of the 6-substituent is regenerated by hydrolysis of the acetal or ketal to remove the protecting group. The Z—W substituent is then introduced by the reaction of the carbonyl group with a Wittig reagent as previously described. The carbonyl group at the 1-position of the tetralone ring reacts relatively slowly with Wittig reagents, thus allowing preferential reaction at the 6-substituent. However, if desired, increased yields at the (Z—W)-substituted tetralone can be obtained by first protecting the carbonyl group at the 1-position, for example by formation of a ketal.

It will be understood that compounds of formulae I, II and III contain asymmetric centers at the 6a and/or 10a-positions. There may be additional asymmetric centers in the 3-position substituent Z—W, the 6-position and the 9-position. Diastereomers with the 9β-configuration are generally favored over the 9α-isomers because of greater (quantitatively) biological activity. For the same reason, the trans(6a,10a)diastereomers of compounds of formula I are generally favored over the cis (6a,10a)diastereomers. Among the enantiomers of a given compound, one will generally be favored over the other and the racemate because of its greater activity. The enantiomer favored is determined by the procedures described below herein. For convenience, the formulae shown in the specification and claims hereof depict the racemic compounds. However, these formulae are considered to be generic to and embracive of the racemic modifications of the compounds of this invention, the diastereomeric mixtures, the pure enantiomers and diastereomers thereof. The utility of the racemic mixtures, the diastereomeric mixtures as well as of the pure enantiomers and diastereomers is determined by the biological evaluations described below.

The compounds of formulae I and II of the present invention are active analgesic agents via oral and parenteral administration and are conveniently administered in composition form. Such compositions include a pharmaceutical carrier selected on the basis of the chosen route of administration and standard pharmaceutical practice. For example, they may be administered in the form of tablets, pills, powders or granules containing such excipients as starch, milk sugar, certain types of clay, etc. They may be administered in capsules, and in mixtures with the same or equivalent excipients. They may also be administered in the form of oral suspensions, solutions, emulsions, syrups and elixirs which may contain flavoring or coloring agents. For oral administration of the therapeutic agents of this invention, tablets or capsules containing from about 0.01 to about 100 mg are suitable for most applications. The physician will determine the dosage which will be most suitable for an individual patient and it will vary with the age, weight and response of a particular patient and the route of administration. Generally, however, the initial analgesic dosage in adults may range from 0.01 to 500 mg per day in single or divided doses. In many instances, it is not necessary to exceed 100 mg daily. The favored oral dosage range is from about 0.01 to about 300 mg per day; the preferred range is from about 0.10 to about 50 mg per day. The favored parenteral dose is from about 0.01 to about 100 mg per day; the preferred range is from about 0.01 to about 20 mg per day.

The analgesic properties of the compounds of this invention are determined by tests using nociceptive stimuli.

TESTS USING THERMAL NOCICEPTIVE STIMULI

(a) Mouse Hot Plate Analgesic Testing

The method used is modified after Woolfe and MacDonald, *J. Pharmacol. Exp. Ther.*, 80, 300–307 (1944). A controlled heat stimulus is applied to the feet of mice on a ⅜" thick aluminum plate. A 250 watt reflector infrared heat lamp is placed under the bottom of the aluminum plate. A thermal regulator, connected to thermistors on the plate surface, programs the heat lamp to maintain a constant temperature of 57° C. Each mouse is dropped into a glass cylinder (6½" diameter) resting on the hot plate, and timing is begun when the animal's feet touch the plate. The mouse is observed at 0.5 and 2 hours after treatment with the test compound for the first "flicking" movements of one or both hind feet, or until 10 seconds elapse without such movements. Morphine has an $MPE_{50}=4$–5.6 mg./kg. (s.c.).

(b) Mouse Tail Flick Analgesic Testing

Tail flick testing in mice is modified after D'Amour and Smith, *J. Pharmacol. Exp. Ther.*, 72, 74–79 (1941), using controlled high intensity heat applied to the tail. Each mouse is placed in a snug-fitting metal cylinder, with the tail protruding through one end. This cylinder is arranged so that the tail lies flat over a concealed heat lamp. At the onset of testing, an aluminum flag over the lamp is drawn back, allowing the light beam to pass through the slit and focus onto the end of the tail. A timer is simultaneously activated. The latency of a sudden flick of the tail is ascertained. Untreated mice usually react with 3–4 seconds after exposure to the lamp. The end point for protection is 10 seconds. Each mouse is tested at 0.5 and 2 hours after treatment with morphine and the test compound. Morphine has an $MPE_{50}$ of 3.2–5.6 mg./kg. (s.c.).

(c) Tail Immersion Procedure

The method is a modification of the receptacle procedure developed by Benbasset, et al., *Arch. Int. Pharmacodyn.*, 122, 434 (1959). Male albino mice (19–21 g.) of the Charles River CD-1 strain are weighed and marked for identification. Five animals are normally used in each drug treatment group with each animal serving as its own control. For general screening purposes, new test agents are first administered at a dose of 56 mg./kg. intraperitonally or subcutaneously, delivered in a volume of 10 ml./kg. Preceeding drug treatment and at 0.5 and 2 hours post drug, each animal is placed in the cylinder. Each cylinder is provided with holes to allow for adequate ventilation and is closed by a round nylon plug through which the animal's tail protrudes. The cylinder is held in an upright position and the tail is completely immersed in the constant temperature waterbath (56° C.). The endpoint for each trial is an energetic jerk or twitch of the tail coupled with a motor response. In some cases, the endpoint may be less vigorous post drug. To prevent undue tissue damage, the trial is terminated and the tail removed from the waterbath within 10 seconds. The response latency is recorded in seconds to the nearest 0.5 second. A vehicle control and a standard of known potency are tested concurrently with screening candidates. If the activity of a test agent has not returned to baseline values at the 2-hour testing point, response latencies are determined at 4 and 6 hours. A final measurement is made at 24 hours if activity is still observed at the end of the test day.

TEST USING CHEMICAL NOCICEPTIVE STIMULI

Suppression of Phenylbenzoquinone Irritant-Induced Writhing

Groups of Carworth Farms CF-1 mice are pretreated subcutaneously or orally with saline, morphine, codeine or the test compound. Twenty minutes (if treated subcutaneously) or fifty minutes (if treated orally) later, each group is treated with intraperitoneal injection of phenylbenzoquinone, an irritant known to produce abdominal contractions. The mice are observed for 5 minutes for the presence or absence or writhing starting 5 minutes after the injection of the irritant. $MPE_{50}$'s of the drug pretreatments in blocking writhing are ascertained

TESTS USING PRESSURE NOCICEPTIVE STIMULI

Effect on the Haffner Tail Pinch Procedure

A modification of the procedure of Haffner, *Experimentelle Prufung Schmerzstillener. Mittel Deutch Med. Wschr.*, 55, 731–732 (1929) is used to ascertain the effects of the test compound on aggressive attacking responses elicited by a stimulus pinching the tail. Male albino rats (50–60 g.) of the Charles River (Sprague-Dawley) CD strain are used. Prior to drug treatment, and again at 0.5, 1, 2 and 3 hours after treatment, a Johns Hopkins 2.5-inch "bulldog" clamp is clamped onto the root of the rat's tail. The endpoint at each trail is clear attacking and biting behavior directed toward the offending stimulus, with the latency for attack recorded in seconds. The clamp is removed in 30 seconds if attacking has not yet occurred, and the latency of response is recorded as 30 seconds. Morphine is active at 17.8 mg./kg. (i.p.).

TESTS USING ELECTRICAL NOCICEPTIVE STIMULI

The "Flinch-Jump" Test

A modification of the flinch-jump procedure of Tenen, *Psychopharmacologia*, 12, 278–285 (1968) is used for determining pain thresholds. Male albino rats (175–200 g.) of the Charles River (Sprague-Dawley) CD strain are used. Prior to receiving the drug, the feet of each rat are dipped into a 20% glycerol/saline solution. The animals are then placed in a chamber and presented with a series of 1-second shocks to the feet which are delivered in increasing intensity at 30-second intervals. These intensities are 0.26, 0.39, 0.52, 0.78, 1.05, 1.31, 1.58, 1.86, 2.13, 2.42, 2.72 and 3.04 mA. Each animal's behavior is rated for the presence of (a) flinch, (b) squeak and (c) jump or rapid forward movement at shock onset. Single upward series of shock intensities are presented to each rat just prior to, and at 0.5, 2, 4 and 24 hours subsequent to drug treatment.

Results of the above tests are recorded as percent maximum possible effect (% MPE). The % MPE of each group is statistically compared to the % MPE of the standard and the predrug control values. The % MPE is calculated as follows:

$$\% MPE = \frac{\text{test time} - \text{control time}}{\text{cutoff time} - \text{control time}} \times 100$$

For example, the analgesic properties of compounds of formulae I and II have been determined according to the above-described procedures with the results shown in Table 1.

TABLE 1

| Compound | MPE$_{50}$ (mg./kg. s.c.) | | | | Time (hr) |
|---|---|---|---|---|---|
| | PBQ | TF | HP | RTC | |
| Trans-6a,10a-1-hydroxy-3-(5'-phenyl-2'-pentyloxy)-6,6-dimethyl-5,6,6a,7,8,9,10,10a,-octahydrophenanthren-9-β-ol | 0.78 | — | — | — | 0.33 |
| | | 3.3 | 29%@10 | — | 0.5 |
| | | 1.3 | 2.5 | 1.1 | 2.0 |
| | | 1.5 | 1.9 | 0.74 | 4.0 |
| | | — | — | 0.66 | 6.0 |
| | | 3.5 | 6.4 | 0.88 | 8.0 |
| | | 2.2 | 27%@10 | — | 24.0 |
| Trans-6a,10a-1-hydroxy-3-(5'-phenyl-2'-pentyloxy)-6,6-dimethyl-5,6,6a,7,8,9,10,10a-octahydrophenanthren-9-one | 10 | — | — | — | 0.33 |
| | | * | * | — | 0.5 |
| 1-hydroxy-3-(5'-phenyl-2'-pentyloxy)-5,6,6a,7,8,9,10,10a-octahydrophenanthren-9-ol | 0.32–0.56 | — | — | — | |
| | | | | | 0.33 |
| | | 1.6 | — | — | 0.5 |
| | | 2.7 | 10 | — | 1.0 |
| | | 11.4 | — | — | 2.0 |
| 1-hydroxy-3-(5'-phenyl-2'-pentyloxy)-5,6,6a,7,8,9,10,10a-octahydrophenanthren-9-one | 17.8–56 | — | — | — | 0.33 |
| Morphine | 0.8 | — | — | — | 0.33 |
| | | 3.2–5.6 | 4–5.6 | — | 0.5 |

PBQ = p-biphenylquinone writhing test
TF = Tail Flick test
HP = Hot Plate test
RTC = Rat Tail Clamp test
Time = Time interval between administration of the drug and measurement of the analgesic affect in the above analgesic test procedures.
* = Inactive at 10

Antihypertensive utility is determined by their ability to lower the blood pressure of conscious hypertensive rats and dogs a statistically significant degree when administered to said hosts at dosages equivalent to those described previously for use as analgesics.

Tranquilizer activity is demonstrated by oral administration to rats at doses of from about 0.01 to 50 mg./kg. with subsequent decreases in spontaneous motor activity. The daily dosage range in mammals is from about 0.01 to about 100 mg.

The use of compounds of the present invention for the treatment of glaucoma is believed to be due to their ability to reduce intraocular pressure. Their effects on intraocular pressure are determined by tests on dogs. The test drug is instilled into the eye of a dog in the form of a solution or is administered systemically at various periods of time after which the eye is anesthetized by instillation of tetracaine hydrochloride, ½%, 2 drops. A few minutes after this local anesthesia, intraocular pressure readings are taken with a Schiotz mechanical tonometer and, after fluoroescein dye is administered, with a Holberg hand application tonometer. The test drug is conveniently used in a solution such as the following: test drug (1 mg.), ethanol (0.05 ml.). Tween 80 (polyoxyalkylene derivative of sorbitan mono-oleate, available from Atlas Powder Co., Wilmington, Delaware 19899) (50 mg.) and saline (to make 1 ml.), or in a more concentrated solution wherein the ingredients are present in proportions of 10 mg., 0.10 ml., 100 mg. and 1 ml., respectively. For human use, concentrations of drug from 0.01 mg./kg. to 10 mg./kg. are useful.

Activity as diuretic agents is determined by the procedure of Lipschitz et al., J. Pharmacol., 79, 97 (1943) which utilizes rats as the test animals. The dosage range for this use is the same as that noted above with respect to the use of the herein described compounds as analgesic agents.

Gastric antisecretory activity is determined by tests on overnight fasted, conscious Heidenhain pouch dogs using pentagastrin, histamine or food to stimulate acid output. Pentagastrin or histamine is administered as a continuous infusion into a superficial leg vein at doses earlier determined to stimulate near maximal acid output from the gastric pouch. Food stimulus consists of one-half can of Ken-L-Ration (approx. 220 L g.) per dog; dogs weighing 9–12.5 kg. are used. Gastric juice is collected at 30 minute intervals following the start of a histamine or pentagastrin infusion or the ingestion of a standard food meal. A total of ten collections are made for each dog during an experiment. Drug is administered orally at levels of from 0.01 to 50 mg./kg. after the third gastric juice collection. All sample volumes are recorded and acid concentration is determined by titrating sample aliquots (1.0 ml.) to pH 7.4 with 0.1 N NaOH using a pH meter (Radiometer) and autoburette. The drug is given orally after placing it in gelatin capsules.

Immunosuppressant activity is evaluated by means of a mixed lymphocyte culture assay procedure. This assay measures the effects of the test compounds on antigen-stimulated lymphocyte proliferation. Spleen lymphoid cells from BALB/C and C57BL/6 mice, $8 \times 10^6$ cells from each strain, are suspended in 2.0 ml. of a serum-free medium containing the test compound and incubated at 37° C. in a 10% carbon dioxide atmosphere. The culture conditions and technique are described by R. W. Dutton in J. Exp. Med., 122, 759 (1965) and the cellular medium is described by W. T. Weber in J. Retic. Soc., 8, 37 (1970). Half of the medium, 1 ml., is replaced with fresh medium every 24 hours. $^3$H-TdR incorporation (24 hour pulse) into desoxyribonucleic acid is then determined by trichloroacetic acid precipitation of desoxyribonucleic acid and assessment of radioactivity in a liquid scintillation counter. The percent inhibition is determined by comparing each test compound-treated mixed culture with the control mixed culture.

The present invention is further illustrated by the following examples. It should be noted, however, that the invention is not limited to the specific details of these examples.

EXAMPLE 1

2-Hydroxymethylene-3,3-dimethyl-6-(5'-phenyl-2'-pentyloxy)-8-benzyloxy-1-tetralone A solution of 258 mg (0.58 mmoles) of 3,3-dimethyl-6(5'-phenyl-2'-pentyloxy)-8-benzyloxy-1-tetralone in 2.5 ml of ethyl formate was added dropwise to 144 mg (3.0 mmoles) of 50% sodium hydride (washed with pentane) and after dilution with 10 ml of ether was stirred overnight at room temperature. The reaction mixture was poured into an ice cold mixture of 1 N hydrochloric acid and ether, the ether layer was separated, and the aqueous was extracted once with ether. The combined ether layers were washed with water (2x), dried (brine, magnesium sulfate), and concentrated to give 257 mg (94%) of the desired compound as a yellow oil.

NMR: CDCl$_3$ (TMS); δ: 16.0 (D, 1H, J=8 Hz, hydroxylic), 7.8 (D, 1H, J=8 Hz, vinyl), 7.7–7.0 (M, 10H, phenyls), 6.4–6.2 (M, 2H, aromatic), 6.2 (S, 2H, benzyloxy methylene), 4.7–4.1 (M, 1H, methane), 2.9–2.4 (M, 5H, benzylmethylene), 2.0–1.5 (M, 4H, ethylene), 1.3 (D, 3H, α-methyl), 1.2 (S, 6H, gem-dimethyl).

EXAMPLE 2

2-(3'-oxobutyl)-2-formyl-3,3-dimethyl-6-(5'-phenyl-2-40 -pentyloxy)-8-benzyloxy-1-tetralone A 257 mg portion of (0.55 mmoles) of 2-hydroxymethylene-3,3-dimethyl-6-(5'-phenyl-2'-pentyloxy)-8-benzyloxy-1-tetralone suspended in 1 ml methanol was stirred with 0.08 ml of methyl vinyl ketone and 0.018 ml triethylamine for 2.5 days at room temperature. The reaction mixture was diluted with ether, washed four times with an aqueous solution of 10% sodium carbonate, and after drying (brine, magnesium sulfate), the ether layer was concentrated to give a yellow oil which was chromatographed on 15 g of silica gel eluted with ether/pentane (1:1). Combination and concentration of the appropriate fractions gave 99 mg (33.5%) of the desired compound as an oil.

EXAMPLE 3

1-Benzyloxy-3-(5'-phenyl-2-'-pentyloxy)-6,6-dimethyl-6a,7,8,9-tetrahydrophenanthren-9-one A 99 mg (0.183 mmoles) portion of 2-(3'-oxobutyl)-2-formyl-3,3-dimethyl-6-(5'-phenyl-2'-pentyloxy)-8-benzyloxy-1-tetralone dissolved in 1 ml of methanol was reacted with 0.18 ml of 2 N potassium hydroxide in methanol at 0° C. After stirring 1.5 hours, the reaction mixture was diluted with 1.36 ml of methanol and treated with an additional 2.36 ml of 2 N potassium hydroxide in methanol and heated to reflux, under nitrogen atmosphere, overnight. The reaction mixture was neutralized at room temperature with acetic acid, concentrated to a solid residue, and taken up in a mixture of ether-water. The ether layer was separated and the aqueous layer was extracted twice more with ether. The combined ether extracts were washed twice with saturated sodium bicarbonate, dried (brine, magnesium sulfate), and concentrated to an oil, which was chromatographed on 5 g silica gel eluted with ether/pentane (1:1). Combination and concentration of the appropriate fractions gave 51 mg (56%) of the desired tri-cyclic compound as an oil.

NMR: CDCl$_3$; δ: 7.6–6,9 (M, 11H, phenyls and vinylic), 6.3 and 6.2 (two D, 2H, J=2 Hz, aromatic), 5.1 (S, 2H, benzyloxy methylene) 1.1 and 0.8 (2S, 6H, gem-dimethyl).

EXAMPLE 4

Trans-6a,10a-1-hydroxy-3-(5'-phenyl-2'-pentyloxy)-6,6-dimethyl-5,6,6a,7,8,9,10,10a-octahydrophenanthren-9-one 55 ml of ammonia was liquified in a flame-dried apparatus placed into a dry ice/acetone bath. A piece of lithium wire was then dissolved in the ammonia to produce a deep blue colored solution and 276 mg (0.55 mmoles) of 1-benzyloxy-3-(5'-phenyl-2'-pentyloxy)-6,6-dimethyl-6a,7,8,9-tetrahydrophenanthren-9-one dissolved in 7 ml of dry tetrahydrofuran was slowly added after which the mixture was stirred for 10 minutes at −80° before solid ammonium chloride was carefully added until all the blue color disappeared. The liquid ammonia was evaporated and 75 ml of water was added to the residue which was then extracted with ether (4×50 ml). The ether extracts were combined, dried (brine, magnesium sulfate), filtered and concentrated to give a red oil which was chromatographed on 90 g of silica gel eluted with 25% ether/hexane. Similar fractions were combined and concentrated to give 76 mg (34%) of the desired trans-isomer as an oil.

NMR: 100 MHz; CDCl$_3$ δ: 7.5–7.0 (m, 6H, phenyl and phenolic); 6.3 and 6.1 (two doublets, 2H, aromatic); 4.0 (broad doublet, 1H); 1.3 (d, 3H, methyl); 1.1 and 0.7 (two singlets, 6H, gem-dimethyl).

Mass spectrum: m/e=406

EXAMPLE 5

Trans-6a,10a-1-hydroxy-3-(5'-phenyl-2'-pentyloxy)-6,6-dimethyl-5,6,6a,7,8,9,10,10a-octahydrophenanthren-9-β-ol Under a nitrogen atmosphere, 12 mg of sodium borohydride was carefully added to a cold solution of the trans-6a-10a-1-hydroxy-3-(5'-phenyl-2'-pentyloxy)-6,6-dimethyl-5,6,6a,7,8,9,10,10a-octahydrophenanthren-9-one in 4 ml of a absolute ethanol and stirred for 1.5 hours before the mixture was poured into 40 ml of cold 5% hydrochloric acid and extracted with ether (4×40 ml). The combined ether layers were washed once with 50 ml of saturated sodium bicarbonate, dried (brine, magnesium sulfate), filtered, and concentrated to a clear colorless oil which was chromatographed on 25 g of silica gel eluted with 1:1 ether/hexane followed by ether. Combination and concentration of the desired fractions gave 38 mg (56.5%) of the pure trans-9-β-hydroxy product as an oil.

NMR: 100 MHz; CDCl$_3$ δ: 7.3–7.0 (m, 5H, phenyl); 6.0 (doublet of doublets; 2H, aromatic); 0.9 and 0.6 (two singlets, 6H, gem-dimethyls); 2.8–1.0 (m, remaining protons).

High-resolution mass spectrum calc m/e: $C_{27}H_{36}O_3$; 408.2676; found m/e 408.2688.

EXAMPLE 6

2-Hydroxymethylene-6-(5'-phenyl-2'-pentyloxy)-8-benzyloxy-1-tetralone

A solution of 2.2 g (5.3 mmoles) of 6-(5'-phenyl-2'-pentyloxy)-8-benzyloxy-1-tetralone in 25 ml of ethyl formate was added dropwise to 0.64 g (26.5 mmoles) of 50% sodium hydride (washed with pentane) and after dilution with 30 ml of ether was stirred overnight at room temperature. The reaction mixture was poured into an ice cold mixture of 1 N hydrochloric acid and ether, the ether layer was separated, and the aqueous was extracted once with ether. The combined ether layers were washed twice with water, dried (brine, magnesium sulfate), and concentrated to give a yellow oil which was chromatographed on 120 g of silica gel eluted with 4:1 hexane/ethylacetate. Combination and concentration of the appropriate fractions gave 1.69 g; (72%) of the desired compound as an oil.

NMR: CDCl$_3$; δ: 1.3 (d, 3H, side chain methyl); 1.7 & 2.6 (M, 10H, methylene); 4.4 (broad singlet, 1H, methine); 5.2 (S, 2H, benzylic); 6.3 (M, 2H, aromatic); 7.2 (S and 8.1–7.2(M), 12H, hydroxyl, vinyl and aromatic).

High resolution mass spectrum:
 calc. m/e 443.2222
 found m/e 443.2218

EXAMPLE 7

2-(3'-oxobutyl)-6-(5'-phenyl-2'-pentyloxy-8-benzyloxy-1-tetralone

A 1.69 g portion (3.8 mmoles) of 2-hydroxymethylene-6-(5'-phenyl-2'-pentyloxy)-8-benzyloxy-1-tetralone suspended in 10 ml methanol was stirred with 0.46 ml of methyl vinyl ketone and 0.13 ml triethylamine for 24 hours at room temperature. The reaction mixture was mixed with ether, washed four times with an aqueous solution of 10% sodium carbonate, and after drying (brine, magnesium sulfate), the ether layer was concentrated to give 1.81 g (98%) of the desired compound as an oil.

High resolution mass spectrum: m/e 484

In an alternative synthetic route, the desired 2-(3'-oxobutyl)-6-(5'-phenyl-2'-pentyloxy)-8-benzyloxy-1-tetralone was obtained by reaction of 6-(5'-phenyl-2'-pentyloxy)-8-hydroxy-1-tetralone with ethyl acetate according to the procedure of Example 6 to give 2-hydroxymethylene-6-(5'-phenyl-2'-pentyloxy)-8-hydroxy-1-tetralone in 98% yield.

Reaction of the latter with methyl vinyl ketone as described above yielded 2-(3'-oxobutyl)-6-(5'-phenyl-2'-pentyloxy)-8-hydroxy-1-tetralone in 55% yield. The desired 2-(3'-oxobutyl)-6-(5'-phenyl-2'-pentyloxy)-8-benzyloxy-1-tetralone was formed in 21% yield from reaction of the 8-hydroxy compound with sodium hydride in dry dimethyl formamide followed by the addition of benzyl bromide at 0° C.

2-hydroxymethylene-6-(5'-phenyl-2'-pentyloxy)-8-hydroxy-1-tetralone: NMR: $CDCl_3$; δ: 1.25 (d, 3H, side chain methyl); 1.8 (m, 6H, methylene); 2.6 (m, 5H, methylene); 4.4 (m, 1H, methine); 6.2 (S, 2H, aromatic); 7.2 (S, 6H, aromatic & vinyl); 12.2 (S, 1H, hydroxyl).

MS: m/e—352

2-(3'-oxobutyl)-6-(5'-phenyl-2'-pentyloxy)-8-hydroxy-1-tetralone: NMR: $CDCl_3$; δ: 1.3 (d, 3H, side chain methyl); 1.6–3.0 (m, 17H, methylene and methyl); 4.4 (m, 1H, methine); 6.2 (S, 2H, aromatic); 7.2 (S, 6H, aromatic & vinyl); 12.8 (S, 1H, hydroxyl).

High resolution mass spectrum:
calc. m/e—394.2144
found m/e —394.2132

EXAMPLE 8

1-Benzyloxy-3-(5'-phenyl-2'-pentyloxy)-5,6,6a,7,8,9-hexahydrophenanthren-9-one A 1.8 g (3.7 mmoles) portion of 2-(3'-oxobutyl)-6-(5'-phenyl-2'-pentyloxy)-8-benzyloxy-1-tetralone was reacted with 40 ml 2 N potassium hydroxide in 40 ml of methanol at 0° C. for 0.5 hours before the mix was heated to reflux, under nitrogen atmosphere, overnight. The reaction mixture was neutralized at room temperature with acetic acid, and taken up in a mixture of ether-water. The ether layer was separated and the aqueous layer was extracted twice more with ether. The combined ether extracts were washed twice with saturated sodium bicarbonate, dried (brine, magnesium sulfate), and concentrated to an oil 1.7 g (90%) which was used without further purification.

NMR: $CDCl_3$; δ: 1.2 (d, 3H, side chain methyl); 1.65, 2.0, 2.6, 4.0 (broad multiplets, 14H, methylene); 4.4 (M, 1H, methine); 5.1 (S, 2H, benzylic); 6.2 (S, 2H, aromatic); 7.3 (M, 10H, aromatic).

High resolution mass spectrum:
calc. m/e 466.2508
found m/e 466.2478

EXAMPLE 9

1-hydroxy-3-(5'-phenyl-2'-pentyloxy)-5,6,6a,7,8,9,10,10a-octahydrophenanthren-9-one and octahydrophenanthren-9-ol 100 ml of ammonia was liquified in a flame-dried apparatus placed into a dry ice/acetone bath. A piece of lithium wire was then dissolved in the ammonia to produce a deep blue colored solution and 1.7 g (3.64 mmoles) of the 1-benzyloxy-3-(5'-phenyl-2'-pentyloxy)-5,6,6a,7,8,9-hexahydrophenanthren-9-one dissolved in 25 ml of dry tetrahydrofuran was slowly added after which the mixture was stirred for 10 minutes at −80° before solid ammonium chloride was carefully added until all the blue color disappeared. The liquid ammonia was evaporated and 75 ml of water was added to the residue which was then extracted with ether (4×50 ml). The ether extracts were combined, dried (brine, magnesium sulfate), filtered and concentrated to give an oil which was chromatographed on 200 g of silica gel eluted with 3:1 cyclohexane/ethyl acetate. Combination and concentration of similar fractions gave 69 mg (5%) of isomeric 9-ketone-compounds as well as 634 mg (46%) of isomeric 9-hydroxy compounds.

9-keto compounds:
$R_f$ in 1:1 acetate/hexane: $R_f$: 0.614 (silica gel)
NMR: $CDCl_3$; δ: 1.35 (d, 3H, side chain methyl); 1.5–3.4 (broad absorption 18H, methylenes); 3.8 (bS, 1H, hydroxyl); 4.4 (S, 1H, methine); 6.3 (d, 2H, aromatic); 7.3 (M, 5H, aromatic).

High resolution mass spectrum:
calc. m/e 378.2195
found m/e 378.2181

9-hydroxy compounds:
$R_f$ in 1:1 ethyl acetate/hexane: 0.283 (silica gel)
NMR: $CDCl_3$; δ: 1.35 (d, 3H, side chain methyl); 1.5–3.4 (broad absorption, 18H, methylenex); 3.6 (m), 3.95 (bS) and 4.3 (M), 4H, methines and hydroxyls; 6.2 (d, 2H, aromatic); 7.3 (M, 5H, aromatic).

High resolution mass spectrum:
calc. m/e 380.332
found: m/e 380.2336

EXAMPLE 10

Other compounds of formulae I, II and III having other substituents for $R_1$, $R_2$, $R_3$, $R_4$, Z and W, as described above herein, may be prepared by the methods of Examples 1 through 5 and Examples 6 through 9 from appropriately substituted tetralones of formula IV.

The substituted tetralones of formula IV may be prepared by the methods shown in Examples 11 through 43.

EXAMPLE 11

3,5-Dimethoxybenzylchloride

Over a period of 20 minutes a solution of 150 g (1.26 moles) of thionyl chloride in 0.65 l of ether was added to 100 g (0.59 moles) of 3,5-dimethoxybenzyl alcohol and 6.6 ml of pyridine in 1.35 l of ether. After stirring for 3 hr the solution containing the product was separated from the residual dark oil, concentrated, and the crude product was redissolved in 1 l of ether, washed with water (3×250 ml), dried (brine, magnesium sulfate), filtered, and reconcentrated to give a dark oil which was vacuum distilled; b.p. 115°–118° C. at 0.4 mm Hg. Upon standing, fractions containing the desired compound solidified to give b 95.3 g (86%) of white solid, m.p. 43°–45° C.

EXAMPLE 12

2-Cyano-3,3-dimethyl-3-(3',5'-dimethoxyphenyl)-butyric acid

A tetrahydrofuran solution of 3,5-dimethoxybenzyl magnesium chloride (prepared from 2.05 g (84 mmoles) of powdered magnesium and 15.0 g (80.4 mmoles) of 3,5-dimethoxybenzyl chloride in 300 ml of dry tetrahydrofuran was added dropwise to a solution of 9.23 g (60.3 mmoles) of ethyl isopropylidene cyanoacetate and 0.40 g of cuprous chloride in 25 ml of tetrahydrofuran while maintaining the reaction temperature below 10° C. After the addition was complete, the reaction mixture was warmed to room temperature, stirred overnight and then poured into 300 ml cold saturated aqueous ammonium chloride. The solution was extracted 3 times with 400 ml of ether and the combined extracts were washed 2 times with 400 ml of water, dried (brine, magnesium sulfate) and concentrated to give 19.4 g of an oil which was hydrolyzed by treatment with aqueous ethanolic potassium hydroxide at room temperature for 15 minutes. The reaction mixture was concentrated to remove the ethanol and the resulting residue was taken up in a mixture of 300 ml ethyl acetate and 150 ml water. The ethyl acetate layer was separated and washed with 150 ml of water followed by 100 ml of saturated sodium bicarbonate. Acidification of the combined aqueous solutions with 10% hydrochlorid acid at 0° C. gave an oil which was separated by extracting 4 times with 150 ml of ether. The ether extracts were combined, washed with 150 ml of water, dried (brine, magnesium sulfate), filtered, and concentrated to yield 11.1 g (50%) of the desired compound as an oil.

NMR: $CDCl_3$; δ: 1.1 (S, 3H), 1.2 (S, 3H), 2.7 (S, 2H), 3.4 (S, 1H), 3.7 (S, 6H), 6.3 (S, 3H), 10.0 (S, 1H).

EXAMPLE 13

3,3-Dimethyl-6,8-dihydroxy-1-tetralone

The 2-cyano-3,3-dimethyl-3-(5'-5'-dimethoxyphenyl)butyric acid (11.1 g; 40.1 mmoles) was treated with 170 ml of 48% aqueous hydrogen bromide and 170 ml og glacial acetic acid at reflux overnight. After cooling to room temperature and concentrating, the reaction mixture was treated with 300 ml of water and extracted with ethyl acetate (3×150 ml). The combined extracts were dried (brine, magnesium sulfate) and concentrated to give a dark foam (7.92 g), which was dissolved in a minimum amount of benzene/ethyl acetate and chromatographed on 350 g of silica gel eluted with benzene followed by 20% ethyl acetate/benzene. The fractions containing the desired compound were combined and concentrated to an oil, which crystallized after treatment with hexane, 4.04 g (49%); m.p. 115°–116° C. Recrystallization from ethyl acetate/hexane gave the desired product as light tan needles; m.p. 116°–117° C. ($C_{12}H_{14}O_3$): Calc.: C: 69.89%; H: 6.84%; Fd. C: 70.26%, H: 6.74%.

EXAMPLE 14

3,3-Dimethyl-6-(5'-phenyl-2'-pentyloxy)-8-hydroxy-1-tetralone

A 1.68 g (8.15 mmoles) portion of 3,3-dimethyl-6,8-dihydroxy-1-tetralone and 2.25 g (16.3 mmoles) of potassium carbonate were suspended in 8 ml of dry dimethyl formamide and reacted with 2.17 g (8.97 mmoles) of 5-phenyl-2-pentyl methanesulfonate under nitrogen at 80° C. for 3.5 hours. After cooling to room temperature the reaction was poured into 100 ml of ice water and extracted with ethyl acetate (2×75 ml), acidified with 10% hydrochloric acid and further extracted with ethyl acetate (2×50 ml). The combined organic phases were washed with water (4×40 ml), dried (brine, magnesium sulfate), filtered, and concentrated to a dark oil which was chromatographed on 120 g of silica gel eluted with benzene/hexane (1:1) followed by benzene. Combination and concentration of the proper fractions afforded 2.72 g (96%) of the desired compound as an oil.

NMR: $CDCl_3$; δ: 1.0 (S, 6H gemdimethyl), 1.3 (D, 3H, J=7 Hz, side chain $CH_3$) 1.7 (M, 4H, ethylene), 2.5 (S, 2H, α-methylene), 2.7 (S, 2H, benzyl methylene), 2.7 (M, 2H, benzyl methylene), 4.1–4.6 (M, 1H, methine), 6.1 (M, 2H, aromatic), 7.1–7.2 (M, 5H, aromatic), 13.0 (S, 1H, phenol).

EXAMPLE 15

3,3-Dimethyl-6-(5'-phenyl-2'-pentyloxy)-8-benzyloxy-1-tetralone

A solution of 1.36 g of 3,3-dimethyl-6-(5'-phenyl-2'-pentyloxy)-8-hydroxy-1-tetralone in 7 ml of dry dimethyl formamide was slowly added to 206 mg of pentane washed 50% sodium hydride. After stirring for 1 hr at room temperature, the dark brown mixture was chilled to 2° in an ice bath, treated dropwise with 0.475 ml of benzyl bromide, stirred for 0.5 hrs at 0° C. then warmed to room temperature and stirred for an additional 3 hours before being poured into a mixture of ice cold 1 N hydrochloric acid and ether. The ether layer was separated and the aqueous was extracted once more with ether. The combined organic layers were washed with water, dried (brine, magnesium sulfate) and concentrated to a yellow oil which was chromatographed on 100 g of silica gel eluted with ether/hexane (1:1). Combination and concentration of the appropriate fractions gave 1.26 g (74%) of the desired compound.

NMR: $CDCl_3$; δ: 7.7–6.9 (M, 10H, phenyl aromatics), 6.3 and 6.2 (two one-proton doublets, J=2 Hz, aromatic), 5.1 (S, 2H, benzyloxy methylene), 4.7–4.2 (M, 1H, methine), 2.8 (S, 2H, benzylic methylene) 2.7 (T, 2H, benzylic methylene) 2.5 (S, 2H, benzylic methylene) 2.7 (T, 2H, benzylic methylene) 2.5 (S, 2H, α-methylene) 1.9–1.5 (M, 4H, ethylene) 1.3 (D, J=7 Hz, 2H, methyl) 1.0 (S, 6H, gem-dimethyl).

EXAMPLE 16

6,8-Dimethoxy-1-tetralone

The tetralone was prepared according to the procedure of Huisgen, Seidl, and Wimmer; *Ann.*, 677, 21 (1964), m.p. 58°–61° C., (lit. m.p.-62°–64° C.).

EXAMPLE 17

6,8-Dihydroxy-1-tetralone

The 6,8-dimethoxy-1-tetralone (3.0 g; 14.0 mmoles) was refluxed overnight with 20 ml of 48% aqueous hydrogen bromide and 20 ml of glacial acetic acid. After cooling to room temperature, the reaction mixture was neutralized with a saturated sodium bicarbonate solution and extracted with ethyl acetate. The combined extracts were dried (brine, magnesium sulfate) and concentrated to afford a red solid which upon trituration with ether gave the desired compound as an off-white solid, 1.77 g (71%); m.p. 209°–210° C.

NMR: CDCl$_3$; δ: 2.0 (M, 2H, methylene); 2.6 (M, 4H, methylene); 6.2 (S, 2H aromatic), 9.2 (broad singlet, 1H, hydroxyl) and 12.65 (S, 1H, hydroxyl).

EXAMPLE 18

6-(5'-phenyl-2'-pentyloxy)-8-hydroxyl-1-tetralone

A 1.77 g (9.9 mmoles) portion of 6,8-dihydroxy-1-tetralone and 2.7 g (19.8 mmoles) of potassium carbonate was suspended in 20 ml of dry dimethyl formamide and reacted with 2.6 g (10.8 mmoles) of 5-phenyl-2-pentyl methanesulfonate under nitrogen, at 80° C. for 3.5 hours. After cooling to room temperature the reaction was poured into 100 ml of ice water and extracted with ethyl acetate (2×75 ml), acidified with 10% hydrochloric acid and further extracted with ethyl acetate (2×50 ml). The combined organic phases were washed with water (4×40 ml), dried (brine, magnesium sulfate), filtered and concentrated to a dark oil which are chromatographed on 130 g of silica gel eluted with hexane/ether (1:1). Combination and concentration of the proper fractions afforded 2.3 g; (72%) of the desired compound as an oil.

NMR: CDCl$_3$, δ: 1.4 (d, 3H, side chain methyl); 1.8 and 2.2 (broad absorb.m, 12H, methylene); 4.4 (broad singlet, 1H, methine) 6.2 (S, 2H aromatic); 7.2 (S, 5H, aromatic); 12.65 (S, 1H, hydroxyl).

EXAMPLE 19

6-(5'-phenyl-2'-pentyloxy)-8-benzyloxy-1-tetralone

A solution of 2.3 g of 6-(5'-phenyl-2'-pentyloxy)-8-hydroxy-1-tetralone in 15 ml of dry dimethyl formamide was slowly added to 187 mg of 50% sodium hydride washed with pentane. After stirring for 1 hr at room temperature, the mixture was chilled to 2° in an ice bath, treated dropwise with 0.92 ml of benzyl bromide, stirred for 0.5 hours at 0° C. then warmed to room temperature and stirred overnight before being poured into a mixture of ice cold 1 N hydrochloric acid and ether. The ether layer was separated and the aqueous layer was extracted once more with ether. The combined organic layers were washed with water, dried (brine, magnesium sulfate), and concentrated to an oil which was chromatographed on 120 g of silica gel eluted with hexane/ethyl acetate (3:1). Combination and concentration of the appropriate fractions gave 2.21 g (77%) of the desired compound.

NMR: CDCl$_3$; δ: 1.25 (D, 3H, side chain methyl); 1.75 and 2.1 (M, 6H, methylene) 2.8 (M, 6H, methylene), 4.4 (broad singlet, 1H, methine); 5.2 (S, 2H, benzylic); 6.3 (m, 2H, aromatic); 7.2 (S&M, 10H, aromatic).

EXAMPLE 20

3-Methoxyisophthalaldehydic acid methyl ester

To a −78° to −100° solution of 1.0 mol of 3-methoxyisophthalic acid dimethyl ester in 1–10 l of toluene is slowly added 1.0 mol of diisobutylaluminum hydride as a 1 M solution in n-hexane. The reaction is stirred for 3 hours after the addition and then quenched by the addition of 10 mol of anhydrous methanol. The reaction is allowed to warm to room temperature and stirred until a filterable precipitate forms. The reaction is filtered and the filtrate evaporated to a residue. The residue is purified by crystallization, distillation or chromatography to yield 3-methoxyisophthalaldehydic acid methyl ester.

EXAMPLE 21

3-chloromethyl-5-methoxybenzaldehyde ethylene glycol acetal

A 0.1 mol portion of 3-methoxyisophthalaldehydic acid methyl ester is heated overnight in 200–300 ml of ethylene glycol containing a catalytic amount of p-toluene sulfonic acid. The reaction is cooled, diluted with dilute aqueous sodium bicarbonate and extracted with ether. After drying with anhydrous sodium sulfate the ether exacts are concentrated to yield a mixture of methyl and δ-hydroxy ethyl esters of the acetal. This mixture is dissolved in ether or tetrahydrofuran and added to an excess (0.1 mol) of lithium aluminum hydride in ether. After the reduction is complete the mixture is worked-up by addition of water and 6 N sodium hydroxide to precipitate the inorganic salts. The ether is dried and evaporated to give the crude benzyl alcohol-acetal. This benzyl alcohol-acetal is heated with 150 ml of thionyl chloride in ether with a catalytic amount of pyridine. After evolution of gases is complete the excess thionyl chloride is removed under vacuum. The benzyl chloride is then purified by column chromatography or vacuum distillation.

EXAMPLE 22

3-butyl-6-formyl-8-hydroxy-1-tetralone

The Grignard reagent of 3-chloromethyl-5-methoxybenzaldehyde ethylene glycol acetal is formed and added to ethyl 2-cyano-2-heptenoate (R. Carrie, R. Bougot and B. Potteau, Compt. Rend. 259, 2859 (1964) using procedures described in Example 12. The adduct thus obtained is cyclized to the tetralone, the methoxy ether cleared and the acetal hydrolyzed using the hydrogen bromide procedure described in Example 13.

EXAMPLE 23

3-butyl-6-formyl-8-benzyloxy-1-tetralone

The product of Example 22 is treated with sodium hydride and benzyl bromide according to the procedures described in Example 15.

EXAMPLE 24

3-butyl-6-[6'-(2'-pyridyl)benzyl]-8-hydroxy-1-tetralone

A mixture of 0.015 mol of 2-(5'-bromopentyl)pyridine (J. Krapcho and W. A. Lott, U.S. Pat. No. 2,918,470) and 0.015 mol of triphenylphosphine in 15 ml of xylene is refluxed for 18 hours, cooled to room temperature, filtered and the resulting triphenylphosphonium bromide is washed with ether and dried. Under a nitrogen atmosphere a mixture of 0.011 mol of this triphenylphosphonium bromide in 15 ml of dimethylsulfoxide and 0.011 mol of 3-butyl-6-formyl-8-benzyloxy-1-tetralone in 10 ml of tetrahydrofuran is added dropwise to a slurry of 0.57 g of 50% sodium hydride in 5 ml of tetrahydrofuran while maintaining the temperature at 0°–5°. After the addition is completed the reaction is stirred for another hour at 0°–5°, concentrated under vacuum, diluted with about 60 ml of water and acidified with 6 N hydrochloric acid. The aqueous solution is extracted with benzene to remove the triphenylphosphine oxide and the aqueous layer is made basic and extracted with ethylacetate. Evaporation of the ethylacetate gives the intermediate alkene as an oil. A mixture of this oil, 25 ml of absolute methanol, 0.15 ml of concentrated hydrochloric acid and 0.3 g of 10% palladium on carbon is hydrogenated in a Parr shaker for one day at 55 psi hydrogen. The mixture is filtered through celite and concentrated under vacuum. Addition of ether yields the desired product as the hydrochloride salt, which is filtered off, washed with ether and dried.

The free base is obtained by dissolving the hydrochloride salt in aqueous ethanol adding aqueous sodium bicarbonate, extracting with ethylacetate, drying and removing the solvent under vacuum.

EXAMPLE 25

Methyl 3-acetyl-5-methoxybenzoate

A solution of 0.5 mol of dimethyl 3-methoxy-isophthalate is dissolved in aqueous methanol containing an equivalent amount (0.5 mol) of potassium hydroxide. The reaction is warmed to about 50° C. and stirred until the hydrolysis is complete. Acidification with 6 N hydrochloric acid, extraction with ether, and evaporation of the ether yields the half-ester which is added to 300 ml of thionyl chloride and heated until evolution of sulfur dioxide and hydrogen chloride ceases. The excess thionyl chloride is removed under vacuum and the half-ester-acid chloride is purified by vacuum distillation. A 0.2 mol portion of this compound in 75 ml of ether is added over a 15 minute period to 0.22 mols of a solution of ethoxymagnesiummalonic ester (prepared by the method of Reynolds and Hauser, Org. Syn. Col. Vol. IV, 708 (1963)) while heating at reflux. The mixture is cooled, shaken with dilute sulfuric acid to dissolve the solids, the ether phase separated, the aqueous layer extracted with ether and the combined ether layers washed with water and concentrated. The resulting material is added to a solution of 60 ml of glacial acetic acid, 7.6 ml of concentrated sulfuric acid and 40 ml of water and heated under reflux for 4 hours or until no more carbon dioxide is evolved. The reaction mixture is concentrated and taken up in ether, dried and the ether evaporated to give 3-acetyl-5-methoxybenzoic acid. Reaction of this acid with thionyl chloride, followed by addition of methanol to the acid chloride yields methyl 3-acetyl-5-methoxybenzoate which is purified by vacuum distillation.

EXAMPLE 26

3-chloromethyl-5-methoxyacetophenone ethylene glycol ketal

Methyl 3-acetyl-5-methoxybenzoate is reacted with ethylene glycol followed by reduction with lithium aluminumhydride and converted to the benzyl chloride using the procedures described in Example 21.

EXAMPLE 27

3-methyl-3-ethyl-6-acetyl-8-hydroxy-1-tetralone

The Grignard reagent of 3-chloromethyl-5-methoxyacetophenone ethylene glycol acetal is formed and added to ethyl 2-cyano-3-methyl-2-pentenoate (F. S. Prout et. al., Org. Syn. Col. Vol. IV, 93 (1963)) using the procedures described in Example 12. The adduct obtained is cyclized to the tetralone, the methoxy ether cleaved and the ketal hydrolized using the procedure described in Example 13.

EXAMPLE 28

3-methyl-3-ethyl-6-acetyl-8-benzyloxy-1-tetralone

The product of Example 27 is treated with sodium hydride and benzyl bromide according to the procedures in Example 15.

EXAMPLE 29

3-methyl-3-ethyl-6-[6'-(N-methyl-2'-piperidyl)-2'-pentyl]-8-hydroxy-1-tetralone N-methyl-2-(3'-bromopropyl)-piperidine (W. L. Meyer and N. Sapionchioy, J. Am. Chem. Soc. 86, 3343 (1964)) is converted to the triphenylphosphorone, reacted with the product of Example 28 and catalytically reduced to the desired compound according to the procedures described in Example 24.

EXAMPLE 30

3-ethyl-6-formyl-8-hydroxy-1-tetralone

The Grignard reagent of 3-chloromethyl-5-methoxybenzaldehyde ethylene glycol acetal produced as in Example 21 is formed and added to ethyl 2-cyano-2-pentenoate (F. D. Popp and A. Catals, J. Org. Chem., 26, 2738 (1961)) using procedures described in Example 12. The addition product obtained is cyclized to the tetralone, the methoxy ether cleaved and the acetal hydrolyzed using the aqueous hydrogen bromide procedure described in Example 13.

EXAMPLE 31

3-ethyl-6-formyl-8-benzyloxy-1-tetralone

The product of Example 30 is treated with sodium hydride and benzyl bromide according to the procedure described in Example 15.

EXAMPLE 32

4-cyclohexylbutyloxy chloromethyl ether 4-cyclohexylbutyric acid (Aldrich) is reduced with excess lithium aluminum hydride in ether to yield 4-cyclohexyl-1-butanol (D. S. Hiers and R. Adams, J. Am. Chem. Soc., 48 2385 (1926)) which is chloromethylated with hydrogen chloride and formaldehyde to yield the desired compound.

EXAMPLE 33

3-ethyl-6-cyclohexylbutoxyethyl-8-hydroxy-1-tetralone 4-cyclohexylbutoxymethyl chloride is formed by the method of Example 32, converted to the triphenylphosphorone, reacted with the product of Example 31 and is then reduced catalytically to the desired compound using procedures analogous to those described in Example 24.

EXAMPLE 34

Ethyl 2-cyano-3-benzyl-2-pentenoate 1-phenyl-2-butanonl (0.12 mol) is condensed with ethyl cyanoacetate (0.10 mol) using the procedure of Prout et al (Org. Synth. Coll. Vol. IV, 93, (1963)).

EXAMPLE 35

3-ethyl-3-benzyl-6-formyl-8-hydroxy-1-tetralone

The Grignard reagent of 3-chloromethyl-5-methoxybenzaldehyde ethylene glycol acetal of Example 21 is formed and added to ethyl 2-cyano-3-benzyl-2-pentenoate using the procedures described in Example 12. The adduct obtained is cyclized to the tetralone, the methyl ether cleaved, and the acetal hydrolyzed using the aqueous hydrogen bromide procedure of Example 13.

EXAMPLE 36

3-ethyl-3-benzyl-6-formyl-8-benzyloxy-1-tetralone

The product of Example 35 is benzylated with benzyl bromide as described in Example 15.

EXAMPLE 37

3-ethyl-3-benzyl-6-carbethoxyethyl-8-hydroxy-1-tetralone

Ethyl bromoacetate is converted to the triphenyl phosphorone, reacted with the product of Example 36 and reduced catalytically to the desired compound using procedures analogous to those described in Example 24.

EXAMPLE 38

3-ethyl-4-benzyl-6-(3'-hydroxypropyl)-8-hydroxy-1-tetralone ethylene glycol ketal A 0.05 mol portion of the product of Example 37 is added to 50 ml of ethylene glycol containing 0.1 g of p-toluene sulfonic acid. After heating for 2-3 days the reaction is cooled, neutralized with aqueous sodium bicarbonate and extracted with ether. The ether layer is dried and concentrated. The redisual ketal is added directly to 0.05 mol of lithium aluminumhydride in ether and refluxed. After the reduction is complete the mixture is worked up by the addition of water and 6 N sodium hydroxide to precipitate the inorganic salts. The ether is dried and evaporated to give the crude alcohol-ketal.

EXAMPLE 39

3-ethyl-3-benzyl-6-(3'-mesyloxypropyl)-8-mesyloxy-1-tetralone ethylene glycol ketal 0.03 mol of the product of Example 38 is dissolved in tetrahydrofuran containing 0.12 mol of triethyl amine and cooled to 0°-5°. Methane sulfonyl chloride (0.07 mol) is added dropwise, the reaction allowed to come to room temperature and stirred for another hour. The triethylamine hydrochloride is removed by filtration and the tetrahydrofuran concentrated and the residue is dissolved in chloroform, washed with water, dried and concentrated to the desired product which is used without further purification.

EXAMPLE 40

3-ethyl-3-benzyl-6-(3'-ethyl thiopropyl)-8-hydroxy-1-tetralone

Under a nitrogen atmosphere 0.02 mol of the product of Example 39 was dissolved in 25 ml of dimethyl formamide and 0.04 mol of sodium ethyl mercaptide is added and the mixture stirred at room temperature overnight. The mixture is then heated to 70° for 3 hours, cooled, poured into water, then acidified with aqueous hydrochloric acid and stirred for several hours. Extraction with ethylacetate, drying the extracts and evaporation of the solvent give the crude product which is purified by chromatography.

EXAMPLE 41

3,3-dimethyl-6-(2'-pyridylmethyloxy)-8-hydroxy-1-tetralone

A 1.68 g (8.2 mmol) portion of 3,3-dimethyl-6,8-dihydroxy-1-tetralone prepared as in Example 13 and 2.25 g (16.3 mmol) of potassium carbonate is suspended in 8 ml of dry dimethyl formamide and reacted with 1.25 g (9 mmol) of 2-picolyl chloride under nitrogen at 50°-80° for 4-5 hours. After cooling the reaction mixture is poured into 100 ml of ice-water acidified with hydrochloric acid, made basic with sodium bicarbonate and extracted with chloroform and ethylacetate. The combined organic phases are washed with water, dried (brine and sodium sulfate), filtered and concentrated to an oil is chromatographed to yield the desired product.

EXAMPLE 42

Methyl 3-(1',2'-dimethylheptyl)-5-methoxybenzoate

A mixture of 0.03 mol of 2-bromoheptane and 0.03 mol of triphenylphosphine in 30 ml of xylene is refluxed for 18-24 hours, cooled to room temperature and the resulting triphenyl phosphonium bromide is filtered, washed with ether and dried. A mixture of this material (0.022 mol) dissolved in 30-50 ml of dimethyl sulfoxide under a nitrogen atmosphere and 0.022 mol of methyl 3-acetyl-5-methoxybenzoate formed as in Example 25 in 10 ml of tetrahydrofuran is added dropwise to a slurry of 1.2 g of 50% sodium hydride in 10 ml of tetrahydrofuran while maintaining the temperature at 0°-5°. After the addition is completed the reaction is stirred overnight at room temperature, concentrated under vacuum, diluted with 100-150 ml of water and the product extracted with pentane-ether. The extracts are combined, washed with water, dried and the solvents removed under vacuum. The alkene thus obtained is purified by chromatography on silica gel.

This alkene is dissolved in 50 ml of absolute methanol and 0.3 ml of concentrated hydrochloric acid and hydrogenated for one day at 55 psi of hydrogen on a Parr shaker containing 0.3 g of palladium on carbon. The reaction mixture is then filtered through celite and concentrated under vacuum and chromatographed or vacuum distilled to obtain the desired product.

EXAMPLE 43

3-(1',2'-dimethylheptyl)-5-methoxybenzyl chloride

A 0.01 mol portion of methyl 3-(1',2'-dimethylheptyl)-5-methoxybenzoate is dissolved in tetrahydrofuran and added to 0.01 mole of lithium aluminum hydride in tetrahydrofuran. After the reduction is complete the mixture is worked-up by addition of water and 6 N sodium hydroxide to precipitate the inorganic salts. The tetrahydrofuran is dried and evaporated to give the crude benzyl alcohol. This benzyl alcohol is heated with thionyl chloride following the procedures in Example 11.

What is claimed is:

1. A compound selected from the group consisting of those having the formula

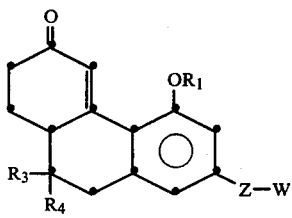

wherein $R_1$ is hydrogen, benzyl, benzoyl, alkanoyl of 1 to 5 carbon atoms or $-CO-(CH_2)_p-NR'R''$ wherein p is 0 or an integer from 1 to 4; each of $R'$ and $R''$ when taken individually is hydrogen or alkyl of 1 to 4 carbon atoms; $R'$ and $R''$ when taken together with the nitrogen to which they are attached form a 5- or 6- membered heterocyclic ring selected from piperidino, pyrrolo, pyrrolidino, morpholino and N-alkylpiperazino having from 1 to 4 carbon atoms in the alkyl group;

$R_3$ is selected from hydrogen, methyl and ethyl;

$R_4$ is selected from hydrogen, alkyl of 1 to 6 carbon atoms and benzyl;

Z is selected from:

(a) alkylene having from one to nine carbon atoms;

(b) $-(alk_1)_m-X-(alk_2)_n-$ wherein each of $(alk_1)$ and $(alk_2)$ is alkylene having from 1 to 9 carbon atoms, with the proviso that the summation of carbon atoms in $(alk_1)$ plus $(alk_2)$ is not greater than 9;

m and n are each 0 or 1;

X is selected from O, S, SO and $SO_2$; and

W is selected from hydrogen, methyl, pyridyl, piperidyl, phenyl, monochlorophenyl, monofluorophenyl and

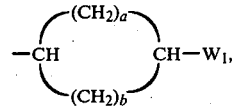

wherein $W_1$ is selected from hydrogen, phenyl, monochlorophenyl and monofluorophenyl; a is an integer from 1 to 5 and b is 0 or an integer from 1 to 4, with the proviso that the sum of a and b is not greater than 5; with the proviso that when $R_1$ is hydrogen, benzyl, benzoyl or said alkanoyl, W is pyridyl or piperidyl.

2. A compound according to claim 1 wherein $R_1$ is hydrogen or alkanoyl; and $R_3$ and $R_4$ are each hydrogen or methyl.

3. A compound according to claim 2 wherein Z is alkylene of 4 to 9 carbon atoms.

4. A compound according to claim 3 wherein Z is $-CH(CH_3)-(CH_2)_3-$.

5. A compound according to claim 3 wherein Z is $-CH(CH_3)-CH(CH_3)-(CH_2)_4-$.

6. A compound according to claim 2 wherein Z is $-(alk_1)_m-X-(alk_2)_n-$.

7. A compound according to claim 6 wherein Z is $-(alk_1)_m-O-(alk_2)_n-$.

8. A compound according to claim 7 wherein Z is $-O-(alk_2)$, wherein $(alk_2)$ has from 4 to 9 carbon atoms.

9. A compound according to claim 8 wherein Z is $-O-CH(CH_3)-(CH_2)_3-$.

* * * * *